United States Patent [19]

Osawa et al.

[11] 4,374,247

[45] Feb. 15, 1983

[54] PROCESS FOR PREPARING 2,2-DISUBSTITUTED THIAZOLIDINES

[75] Inventors: Yasuko Osawa, Tokyo; Saburo Uchikuga, Yokohama, both of Japan

[73] Assignee: Sogo Pharmaceutical Co., Ltd., Sagamihara, Japan

[21] Appl. No.: 156,488

[22] Filed: Jun. 4, 1980

[30] Foreign Application Priority Data

Dec. 7, 1979 [JP] Japan .................................. 54-158130

[51] Int. Cl.$^3$ .................... C07D 277/04; C07D 277/60
[52] U.S. Cl. .................................... 548/146; 548/147; 564/500; 260/458 R
[58] Field of Search ................. 548/146, 147; 564/500

[56] References Cited

U.S. PATENT DOCUMENTS 4,011,233  3/1977  Dubs et al. .......................... 548/146
4,212,826  7/1980  Yamaguchi .......................... 564/500

Primary Examiner—Alton D. Rollins
Attorney, Agent, or Firm—Browdy & Neimark

[57] ABSTRACT

A method for preparing 2,2-disubstituted thiazolidine involves reacting aminoalkyl hydrogen-sulfate with a compound having hydrosulfide ion in the presence of ketone. According to the present method, such thiazolidine can be prepared in good yield and desired purity without using harmful ethylenimine as a starting material.

5 Claims, No Drawings

PROCESS FOR PREPARING 2,2-DISUBSTITUTED THIAZOLIDINES

This invention relates to a novel industrial method for preparing 2, 2-disubstituted thiazolidines safely and in good yield and high purity without causing any pollution.

The compounds of this invention, 2, 2-disubstituted thiazolidines, are particularly useful starting materials for synthesis of cysteamines, for example such as the one represented by the formula $$HS-CH_2-CH_2-NH_2$$

which are useful as radiation protecting substances and intermediates for various medical drugs.

These compounds are represented by the following general formula (I)

$$
\begin{array}{c}
R_3 \quad H \\
R_4-C-N \\
\phantom{R_4-}| \phantom{-N} \diagdown \\
\phantom{R_4-C-}C \phantom{-} R_1 \\
\phantom{R_4-}| \phantom{-N} \diagup \diagdown \\
R_6-C-S \phantom{-} R_2 \\
\phantom{R_4-}| \\
R_5
\end{array}
\quad (I)
$$

Wherein:

$R_1$ and $R_2$ are alkyl group of from one to five carbon atoms or phenyl group, or $R_1$ is joined with $R_2$ to form a ring;

$R_3$, $R_4$, $R_5$ and $R_6$ are hydrogen or lower alkyl group.

Hitherto, 2, 2-dimethyl thiazolidine has been prepared by the reaction of ethylenimine on hydrogen sulfide in the presence of acetone, as illustrated by the following scheme (Ann. Chem. 566 210 (1950)):

$$
\begin{array}{c}
\phantom{xx}\diagup \\
[\phantom{x}]NH + O=C\phantom{x} \\
\phantom{xx}\diagdown \\
\phantom{x}CH_3 \\
\phantom{xx}CH_3
\end{array}
+ H_2S \rightarrow
\begin{array}{c}
\phantom{xx}CH_2-N \phantom{xx} CH_3 \\
\phantom{xxxxx}\diagdown \diagup \\
\phantom{xxxxxxx}C \\
\phantom{xxxxx}\diagup \diagdown \\
\phantom{xx}CH_2-S \phantom{xx} CH_3
\end{array}
+ H_2O
$$

However, the prior method above described has extremely serious drawbacks as follows: in the first place, it is necessary to employ ethylenimine as a starting material. Ethylenimine is high in price and extremely poisonous and as well its is extremely dangerous to handle because of it low boiling point and its causing a vigorous exothermic reaction. Therefore it is particularly difficult to control the reaction especially in the case that it is performed on an industrially large scale. In the second place, it is inevitable that hydrogen sulfide is used in the form of free gas. Hydrogen sulfide, because it is strongly poison and has a foul odor, is not only very difficult to handle but also is a source of air pollution.

That is to say, since the prior method requires these high-priced, poisonous and dangerous starting materials, it has serious drawbacks as follows: hazardousness, delicate control of reaction and problem of air pollution.

It is an object of the invention to provide a novel process for the preparation of 2, 2-disubstituted thiazolidines which does not exhibit the disadvantages of the conventional process and which makes it possible to achieve a high productivity and high purity. It is another object of the invention to provide a novel industrial process without using these high-priced and dangerous starting materials.

In particular, the key to the present invention resides in the novel and very useful discovery that, instead of aziridine, an aminoalkyl hydrogensulfate can be used as starting material for synthesis of thiazolidine corresponding to the formula (I).

Aminoalkyl hydrogensulfates, represented by the following general formula (II)

$$
\begin{array}{c}
\phantom{xx}R_3 \phantom{x} R_5 \\
\phantom{xx}| \phantom{xx} | \\
NH_2-C-C-OSO_3H \\
\phantom{xx}| \phantom{xx} | \\
\phantom{xx}R_4 \phantom{x} R_6
\end{array}
\quad (II)
$$

wherein:

$R_3$, $R_4$, $R_5$ and $R_6$ are hydrogen or lower alkyl, are prepared by reacting 2-amino alkylalcohol with sulfuric acid, and they are low in price and suitable for the starting material of the present process which does not exhibit the disadvantages of the conventional process wherein aziridine has been used as the starting material.

Namely, the present invention is an industrial method of producing 2, 2-disubstituted thiazolidines of the formula (I) in good yield and high purity by reacting the starting material, namely aminoalkyl hydrogensulfate of the formula (II), with a compound containing hydrosulfide ion (−SH) in the presence of Ketone having the following formula (III)

$$
\begin{array}{c}
R_1 \\
\phantom{xx}\diagdown \\
\phantom{xxxx}C=O \\
\phantom{xx}\diagup \\
R_2
\end{array}
\quad (III)
$$

wherein:

$R_1$ and $R_2$ are alkyl group of from one to five carbon atoms or phenyl group, or $R_1$ is joined with $R_2$ to form a ring.

Aminoalkyl hydrogensulfates, which have the formula (II) and are used as the starting material, may be easily prepared in good yield by the dehydration reaction of 2-aminoalkylalcohol (obtained commercially) with sulfuric acid, and are safe, stable and low-priced compounds that differ from azilidine. According to the present invention, all of the compounds of the formula (II) are suitably used, and the preferred esters include, for example, the compounds wherein $R_3$, $R_4$, $R_5$ and $R_6$ are hydrogen or methyl group.

With respect to ketone of the formula (III), all of the compounds corresponding to the formula are suitably used, and the preferred ketones include, for example, the compounds wherein $R_1$ and $R_2$ are straight or branched chain alkyl of 1 to 5 carbons or phenyl, or $R_1$ is joined with $R_2$ to form a ring. As these ketones which are particularly suitable, there may be mentioned: acetone, methyl ethyl ketone, methyl isobutyl ketone, cyclo hexanone, etc. All of them are obtained commercially and therefore they are readily available. The ketone is employed in an amount which is greater than the amount required theoretically. The excess of the ketone is recovered after the completion of reaction and then may be further employed in the reaction for the second time. A heterogeneous reaction may be also conducted with water.

The compounds having hydrosulfide ion (−SH) as used throughout of this specification refer to those which can release the hydrosulfide ion, for example hydrosulfide, sulfide, polysulfide, sulfur, etc. Such compound may be suitably used separately or in combination therewith and even hydrogen sulfide may be used when desired. The following compounds are illustrative: alkali metal salts thereof such as sodium hydrosulfide, potassium sulfide, etc. all of which are readily available. It is preferable that the hydrosulfide ion-containing compound is used in the reaction system in such amount as equivalent or more, preferably from one to two-fold equivalents, of hydrosulfide ion (−SH) based on the amount of aminoalkyl hydrogensulfate. Therefore, it is preferable that, in the reaction system, alkali metal atom be present in an amount twice as much as moles of aminoalkyl hydrogensulfate.

The reaction proceeds at a satisfactory rate at temperatures of from room temperature to 150° C., preferably from 50° to 120° C. The reaction conditions are not critical and the reaction may be suitably carried out under pressure, with stirring or at reflux. The process duration is defined according to the reaction temperature and kind of ketone and generally it varies within the range of from one to ten hours. After the completion of reaction, the by-product of sulfates and unreacted sulfur-compounds are filtered off, the ketone phase wherein the desired product is dissolved is separated from the water phase, followed by the distillation or sublimation, yielding, 2, 2-disubstituted thiazolidines in good yield and high purity.

The following examples further illustrate the invention:

EXAMPLE 1

To a solution of 12.0 g of sodium hydroxide in 20 ml of water, 42.4 g of 2-aminoethyl hydrogensulfate is added, followed by the addition of 48.0 g of sodium hydrosulfide (the content thereof being 70%) and 200 ml of methyl ethyl ketone. The mixture is allowed to react at a temperature of 90° C. for 3 hours in an autoclave.

After completion of the reaction, the reaction mixture is allowed to cool to room temperature, and the precipitate is filtered off. The filtrate is separated into methyl ethyl ketone phase and water phase. The water phase is washed two times with 30 ml of methyl ethyl ketone and then combined with said methyl ethyl ketone phase. Thus combined methyl ethyl ketone phases are concentrated. The residue is distilled under reduced pressure to yield 33.3 g of 2-methyl-2-ethyl thiazolidine having a boiling point of 72.0° C. (at 10 mm. Hg) (yield 84.7%). I. R. and b. p. thereof are identical with those of reference standard.

EXAMPLE 2

Using 12.0 g of sodium hydroxide, 10 ml of water, 42.4 g of 2-aminoethyl hydrogensulfate, 30.0 g of sodium hydrosulfide (70% pure) and 200 ml of one of the six kinds of ketones set forth below, the procedure of Example 1 is respectively repeated to yield respectively corresponding thiazolidines in good yield: acetone, methyl ethyl ketone, methyl isobutyl ketone, cyclohexanone, methyl n-amyl ketone and acetophenone.

The results are shown in the following Table.

| Kind of ketone | Reaction temperature (°C.) | Product | Boiling point (°C.) | Yield (%) |
|---|---|---|---|---|
| Acetone | 75 | 2,2-Dimethyl thiazolidine | 59.3 (at 14.5mmHg) | 56.0 |
| Methyl ethyl ketone | 90 | 2-Methyl-2-ethyl thiazolidine | 72.0 (at 10mmHg) | 82.6 |
| Methyl isobutyl ketone | 110 | 2-Methyl-2-isobutyl thiazolidine | 77.5 (at 6.5mmHg) | 56.3 |
| Cyclohexanone | 120 | Spiro cyclohexane-1,2'-thiazolidine | 94.0 (at 3.5mmHg) | 76.1 |
| Methyl-n-amyl ketone | 120 | 2-Methyl-2-amyl-thiazolidine | 102.5 (at 4.5mmHg) | 52.4 |
| Acetophenone | 120 | 2-Methyl-2-phenyl-thiazolidine | 127.0 (at 3mmHg) | 50.8 |

With respect to each thiazolidine, I. R. and b.p. thereof are respectively identical those of reference standard.

EXAMPLE 3

To a solution of 12.0 g of sodium hydroxide in 20 ml of water, 42.4 g of 2-aminoethyl hydrogensulfate is added, followed by the addition of 36.0 g of sodium hydrosulfide (70% pure), 9.6 g of sulfur powder and 200 ml of methyl ethyl ketone. The mixture is allowed to react for 3 hours at a temperature of 90° C. in an autoclave.

After completion of the reaction, the reaction mixture is allowed to cool to room temperature, and the procedure described in Example 1 is repeated to yield 35.0 g of 2-methyl-2-ethyl thiazolidine (yield 89.1%).

EXAMPLE 4

A mixture, which comprises 42.4 g of 2-aminoethyl hydrogensulfate, 25.2 g of sodium hydrosulfide (70% pure), 82.2 g of sodium sulfide nonahydrate (92% pure) and 200 ml of methyl ethyl ketone, is allowed to react for 1.5 hours at 85° C. in an autoclave.

After completion of the reaction, the reaction mixture is allowed to cool to room temperature, thereafter the procedure described in Example 1 is repeated to yield 24.6 g of 2-methyl-2-ethyl thiazolidine (yield 62.6%).

EXAMPLE 5

A mixture comprising 42.4 g of 2-aminoethyl hydrogensulfate, 25.2 g of sodium hydrosulfide (the content thereof being 70%), 82.2 g of sodium sulfide nonahydrate (the content thereof being 92%) and 200 ml of methyl ethyl ketone is refluxed for a period of 6 hours.

After completion of the reaction, the reaction mixture is cooled to room temperature, and then the operation is conducted under the same conditions as those of Example 1, yielding 23.5 g of 5-methyl-2-ethyl thiazolidine (yield 59.8%).

EXAMPLE 6

A mixture comprising 42.4 g of 2-aminoethyl hydrogensulfate, 82.2 g of sodium sulfide nonahydrate (92% pure), 20 ml of water and 200 ml of methyl ethyl ketone is allowed to react for 1.5 hours at 105° C. in an autoclave.

After completion of the reaction, the reaction mixture is allowed to cool to room temperature, and thereafter 22.6 g of 2-methyl-2-ethyl thiazolidine is produced in the same manner as in Example 1 (yield 57.5%).

EXAMPLE 7

To a solution of 12.0 g of sodium hydroxide in 20 ml of water, 42.4 g of 2-aminoethyl hydrogensulfate, 25.2 g of sodium hydrosulfide (70% purity) and 200 ml of methyl ethyl ketone are successively added. The mixture is stirred for 6 days at room temperature and then thus formed precipitate is filtered off. And thereafter the procedure described in Example 1 is repeated to give 9.7 g of 2-methyl-2-ethyl thiazolidine (yield 24.7%).

EXAMPLE 8

19.8 g of potassium hydroxide and 42.4 g of 2-aminoethyl hydrogensulfate are dissolved in 108.2 g of a 25% solution of potassium hydrosulfide, and 200 ml of acetone is further added thereto. Thus obtained mixture is reacted for a period of 3 hours at a temperature of 75° C. in an autoclave.

The procedure described in Example 1 is repeated to yield 15.4 g of 2, 2-dimethylthiazolidine (yield 43.8%).

EXAMPLE 9

A mixture comprising 42.4 g of 2-aminoethyl hydrogensulfate, 80.8 g of potassium sulfide (43% purity), 20 ml of water and 200 ml of methyl isobutyl ketone is allowed to react for 3 hours at 110° C. in an autoclave.

Thereafter, the procedure described in Example 1 is repeated, yielding 13.9 g of 2-methyl-2-isobutyl thiazolidine (yield 29.1%).

EXAMPLE 10

To a solution of 12.0 g of sodium hydroxide in 20 ml of water, 46.6 g of 1-amino-2-propyl hydrogensulfate is added, followed by the addition of 32.4 g of sodium hydrosulfide (70% purity) and 200 ml of methyl ethyl ketone. Thus formed mixture is allowed to react for 2.5 hours at 90° C. in an autoclave.

After the end of reaction, the reaction mixture is allowed to cool to room temperature, and then the procedure described in Example 1 is repeated to yield 19.7 g of 2, 5-dimethyl-2-ethyl thiazolidine having a boiling point of 67.8° C. at 10 mm Hg (yield 50.0%).

EXAMPLE 11

50.8 g of 2-amino-2-methyl-1-propyl hydrogensulfate is added to a solution of 12.0 g of sodium hydroxide in 20 ml of water. And then 32.4 g of sodium hydrosulfide (70% purity) and 200 ml of methyl ethyl ketone are further added thereto. This obtained mixture is allowed to react for 2.5 hours at 90° C. in an autoclave.

After the end of reaction, the reaction mixture is allowed to cool to room temperature to form precipitate which is removed off by filtration. Thus obtained filtrate is separated into methyl ethyl ketone phase and water phase. The water phase is washed two times with 30 ml of methyl ethyl ketone and all of these methyl ethyl ketone phases are combined therewith. The mixture is concentrated to form a crystal which is filtered. Thus obtained crystal is sublimed under reduced pressure, at 6 mm. Hg, in an oil bath to give 14.3 g of 2, 4, 4-trimethyl-2-ethyl thiazolidine as a white crystal (yield 32.8%).

The crystal has a melting point of 102° C.

EXAMPLE 12

A solution of 24.0 g of sodium hydroxide in 40 ml of water is treated with 10.2 g of hydrogen sulfide with cooling in an ice bath for adsorption thereof. 42.4 g of 2-aminoethyl hydrogensulfate and 200 ml of methyl ethyl ketone are added thereto. Thus obtained mixture is allowed to react for 3 hours at 90° C. in an autoclave.

After the end of reaction, the reaction mixture is allowed to cool to room temperature. Thereafter the procedure described in Example 1 is repeated to yield 26.1 g of 2-methyl-2-ethyl thiazolidine (yield 66.4%).

What is claimed is:

1. A process for preparing a 2,2-disubstituted thiazolidine having the formula

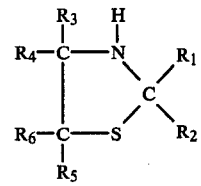

wherein: $R_1$ and $R_2$ are each an alkyl group of from one to five carbon atoms or phenyl group, or $R_1$ is joined with $R_2$ to form a cyclohexane ring; and $R_3$, $R_4$, $R_5$, and $R_6$ are hydrogen or lower alkyl, the process comprising the step of reacting aminoalkyl hydrogensulfate of the formula

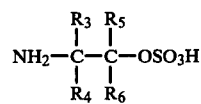

wherein: $R_3$, $R_4$, $R_5$ and $R_6$ are defined above,
with a compound having hydrosulfide ion ($^-$SH) and selected from the group consisting of sodium hydrosulfide, potassium hydrosulfide, sodium sulfide and potassium sulfide,
in the presence of ketone capable of reacting with said aminoalkyl hydrogensulfate to produce said thiazolidine, said ketone having the formula

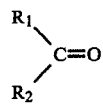

wherein: $R_1$ and $R_2$ are defined above, and thereby obtaining said thiazolidine.

2. The process defined in claim 1 wherein aminoalkyl hydrogensulfate is 2-aminoethyl, 1-amino-2-propyl or 2-amino-2-methyl-1-propyl hydrogensulfate.

3. The process defined in claim 1 wherein said ketone is methyl ethyl ketone, methyl isobutyl ketone, cyclohexanone, methyl n-amyl ketone, acetophenone or acetone.

4. The process defined in claim 1 wherein said process is conducted in the presence of said ketone in an amount which is greater than that required theoretically.

5. The process defined in claim 1 wherein said process is conducted in the presence of said hydrosulfide ion in an amount which is equal to, or greater than, the equivalent amount required to completely react with the amount of aminoalkyl hydrogensulfate employed.

* * * * *